United States Patent [19]

Higo et al.

[11] 4,089,764

[45] May 16, 1978

[54] PROCESS FOR PREPARATION OF β-BOURBONENE

[75] Inventors: Moriaki Higo, Hiratsuka; Hitoshi Saga, Hatano; Yoji Watanabe, Sakura; Kunitomo Suzuki, Ninomiya, all of Japan

[73] Assignee: The Lion Dentifrice Co., Ltd., Tokyo, Japan

[21] Appl. No.: 805,543

[22] Filed: Jun. 10, 1977

[30] Foreign Application Priority Data

Jun. 11, 1976 Japan .................................. 51-68554
Jan. 31, 1977 Japan .................................. 52-9505

[51] Int. Cl.² .............................................. B01J 1/10
[52] U.S. Cl. ............................................. 204/162 R
[58] Field of Search ................................. 204/162 R

[56] References Cited

U.S. PATENT DOCUMENTS 3,560,582  2/1971  Schroder ..................... 204/162 R
3,616,372  10/1971  Kropp ..................... 204/162 R X Primary Examiner—Leland A. Sebastian
Attorney, Agent, or Firm—C. Bruce Hamburg

[57] ABSTRACT

A process for preparing β-bourbonene which comprises irradiating internally or externally an essential oil containing germacrene D, such as ylang-ylang oil, cananga oil, the essential oil of *Solidago altissima* L., the essential oil of *Solidago gigantea Aiton var.* leiophylla Fern., with the light of low pressure or high pressure mercury lamp to obtain β-bourbonene.

8 Claims, No Drawings

PROCESS FOR PREPARATION OF β-BOURBONENE

BACKGROUND OF THE INVENTION

This invention relates to a process for preparing β-bourbonene having a peculiar fragrance which is used as raw material of perfume or for other use, by using, essential oil of Solidago altissima L., ylang-ylang oil or other essential oil containing germacrene D.

β-Bourbonene has attracted attention as a useful raw material of perfume owing to its peculiar fragrance. However, no simple process for preparing β-bourbonene in a large scale with a high yield was developed.

A prior synthetic process for obtaining β-bourbonene by using cyclopentanone as the starting material was proposed [J. Am. Chem. Soc., Vol. 90, 6171 (1968)]. Another process by utilizing photochemical reaction of germacrene D was also proposed [Tetrahedron Letters, No. 27, 2263 (1969)]. But the former process using cyclopentanone as the starting material requires many operations and the yield of β-bourbonene is less than 3%. Moreover, the process has such a serious demerit that it is unpractical because of the necessity of using special chemicals. In the latter process utilizing the photochemical reaction of germacrene D, β-bourbonene is generally obtained by the isolation of germacrene D from essential oil of Pittosprum Tobira and its conversion to β-bourbonene by irradiation with light. But this process has the following unfavourable problems: the procurement of the raw material plant is not easy, processes of isolation and refining of germacrene D are complicated, germacrene D is generally unstable, etc.

A method of manufacturing germacrene D from the essential oil of Solidago altissima L., which is easily available, has also been reported [J. Agr. Chem. Soc., Japan, Vol. 49, 245 (1975)]. However, by this method, germacrene D can only be obtained according to the following complicated operations: The essential oil of Solidago altissima L. is treated by (I) weak alkali, (II) strong alkali, (III) silica gel chromatography, (IV) fractional distillation under reduced pressure, (V) column chromatography on alumina impregnated with silver nitrate, (VI) retreatment under the same condition as of (V). Moreover, this method has the following problems: the yield of germacrene D is as low as about 3%, there is a fear that germacrene D is decomposed during the column chromatography, thermal isomerization of germacrene D is apt to take place during the fractional distillation, and adoption of the chromatography makes the mass treatment of the essential oil inconvenient. For the above mentioned reason, in the application of the process for preparing β-bourbonene by means of light irradiation of germacrene D isolated from the essential oil of Solidago altissima L., the yield of β-bourbonene becomes extremely low and the actual adoption of this process has been difficult.

Another method of manufacturing germacrene D from ylang-ylang oil is reported [Recherches, Vol. 19, 269 (1974)]. According to this method, silver nitrate solution of about 50% in concentration is added to ylang-ylang oil to form a double salt of germacrene D and silver nitrate, and germacrene D of high purity is obtained. This method has the following problems for its application: one mole of expensive silver nitrate is required for the refining one mole of germacrene D, operations are troublesome because above-mentioned treatment should be done in a dark room and because treatment with concentrated aqueous ammonia is required to get free germacrene D from the double salt after the ethanol washing of the double salt.

BRIEF SUMMARY OF THE INVENTION

An object of this invention is to solve the problems of the above-mentioned prior processes and to provide a new simple process for preparation of β-bourbonene in which β-bourbonene can be obtained in great amount with a high yield.

Another object of the invention is to provide a process for preparation of β-bourbonene in which operation is easy and suitable for mass treatment and moreover β-bourbonene can be produced economically.

According to this invention, there is provided a process for preparing β-bourbonene, which comprises irradiating internally or externally an essential oil containing germacrene D, such as ylang-ylang oil, cananga oil, the essential oil of Solidago altissima L., the essential oil of Solidago gigantea Aiton var. leiophylla Fern., with the light of low pressure or high pressure mercury lamp to obtain β-bourbonene.

The inventors have completed this invention after their researches for the establishment of a simplified process for preparing β-bourbonene. Namely, according to the invention, when essential oil containing germacrene D such as the essential oil of Solidago altissima L., ylang-ylang oil, etc., is irradiated directly with the light of high pressure or low pressure mercury lamp, β-bourbonene is formed in considerably high concentration in the irradiated product, and β-bourbonene can be easily isolated from the product by means of popular isolation methods such as fractional distillation under reduced pressure. Accordingly, β-bourbonene can be prepared with a high yield.

These and other objects of the invention will become more apparent in the detailed description and examples which follow.

DETAILED DESCRIPTION

In this invention, the raw material used for preparation of β-bourbonene is the essential oil which contains germacrene D. The following plants are some examples of the plants of which essential oils are usable as the raw material.

| Name of Plant | Part | Amount of germacrene D contained in 100g of essential oil (g) |
|---|---|---|
| Solidago altissima L. | leaf | 40–60 |
| Solidago gigantea Aiton var. leiophylla Fern. | leaf | 40–60 |
| Solidago virgaurea L. subsp. asiatica Kitamura | leaf | 20–40 |
| Canangium odoratum Baill. f. macrophylla (Cananga oil) | flower | 5–10 |
| Canangium odoratum Baill. f. Genuina (Ylang-ylang Oil) | flower | 20–30 |
| Chrysanthemum boreale Makino | | |
| Chrysanthemum makinoi Matsum. et Nakai | total plant | 22 |
| Erigeron annuus L. | total plant | 21 |
| Pinus edulis | flower | 35 |
| | wood(oleo-resin) | 2 |
| Pinus monophylla | wood(oleo-resin) | 0.4 |
| Pelargonium graveolens L. | total plant | 8 |
| Satureja vulgaris L. | leaf | 52 |
| Salvia sclarea | flower, | |

| Name of Plant | Part | Amount of germacrene D contained in 100g of essential oil (g) |
|---|---|---|
| (Clary sage oil) | leaf | 20–30 |

The essential oils containing germacrene D, if they are ylang-ylang oil, cananga oil or other oil which are on the market, can be used as they are. When such oils are not available in market, essential oils can be obtained by means of popular treatment such as expression, extraction and steam distillation.

Namely, essential oils are obtainable by steam-distilling leaves, stalks, flowers, buds or other parts of plants, such as *Solidago altissima L., Solidago gigantea Aiton var. leiophylla Fern., Solidago virgaurea L. subsp. asiatica Kitamura*, after drying the plants at room temperature if necessary. Or, essential oil can be obtained by soaking selected plants in solvents to extract the required components, removing undissolved residue by decantation or by filtration, and then by removing the solvent by such treatment as distillation. In the latter case, where the extraction method is applied, the mixture of essential oil and the solvent may be forwarded, without removing the solvent, to the next step of irradiation with the light of mercury lamp. In the solvent extraction method, petroleum ether, petroleum benzine, ligroin, hexane, cyclohexane, ether, benzene, etc., can be used as solvent. When soaking in solvent and separation of undissolved residue are repeated two to three times, generally almost all essential oil can be extracted.

The essential oil may be diluted, before irradiation process, to an appropriate degree of dilution with at least one polar or non-polar solvent such as petroleum ether, petroleum benzine, ligroin, hexane, cyclohexane, ether, benzene, ethyl acetate, methanol, ethanol, acetone, acetonitrile, water. As has been mentioned above, the mixture of the extracted essential oil and the solvent which has been used for the extraction of the essential oil can be used as raw material. The said mixture may be mixed with the above-mentioned solvents before irradiation process.

The low boiling point component (e.g., monoterpene) may be removed from the essential oil by fractional distillation. The essential oil may also be treated with appropriate alkali, etc., before irradiation process. A mixture of some kinds of essential oil containing germacrene D may be subjected to irradiation with light.

For preparation of $\beta$-bourbonene, the essential oil containing germacrene D or the mixture of the essential oil and the solvent is irradiated with light. Low pressure or high pressure mercury lamp can be used as the light source. Other suitable light source can also be used. Internal or external irradiation is applicable. In the case of irradiation with low pressure mercury lamp, an addition of petroleum ether, hexane, acetone, methanol or ethanol to the essential oil as solvent brings about highly excellent results in the yield of $\beta$-bourbonene and saves irradiation time. In the case of irradiation with high pressure mercury lamp, an addition of methanol, ethanol or acetone to the essential oil as solvent gives better yield of $\beta$-bourbonene and saves irradiation time. In this case, as will be mentioned later, acetone acts as a sensitizer as well and is effective for reduction of irradiation time.

When such ketones as acetone, di-t-butyl ketone, acetophenone, benzophenone, cyclohexanone, menthone, xanthone, anthraquinone, methoxyacetophenone, or such dyes as erythrosine are added as sensitizer by 0.1 to 1000 wt.% of the amount of the essential oil to the essential oil or to the reaction system consisting of the essential oil and the solvent, then irradiation time can be much reduced. Several hundred hours of irradiation time are generally necessary for 100 g of essential oil, but by use of the appropriate solvent mentioned above and/or by addition of the sensitizer, reaction can be completed within a time ranging from some dozen hours up to dozens of hours.

In such a manner, $\beta$-bourbonene can be prepared by means of irradiation with light to the essential oils. The product solution (the essential oil after irradiation process) contains $\beta$-bourbonene as a main component, and also contains sesquiterpenes and monoterpenes.

The product solution can be used as raw material of perfume or flavor. The product solution from which monoterpenes have been removed by distillation under reduced pressure can also be used as raw material of perfume or flavor.

The isolation of $\beta$-bourbonene from the product solution can be easily carried out by fractional distillation of the product solution under reduced pressure. $\beta$-Bourbonene can also be isolated by other conventional methods such as column chromatography.

According to this invention, the ratio of conversion of germacrene D in the essential oil to $\beta$-bourbonene ranges, under general conditions, from 75 to 100%. Namely, almost all of germacrene D in the essential oil is converted to $\beta$-bourbonene. This is much more higher compared to conversion ratio of about 7.5% attained by the prior process of Nii et al. [J. Arg. Chem., Japan, Vol. 49, 245 (1975)]. The yield of $\beta$-bourbonene of about 40% to 60% on the basis of the weight of the essential oil can be achieved in case of using the essential oil of Solidago altissima L.

The $\beta$-bourbonene thus obtained is used as it is as raw material of perfume or for other use. It may be converted to $\alpha$-bourbonene according to a reported method [J. Am. Chem. Soc., Vol. 90, 6171 (1968)].

As has been explained, according to this invention, $\beta$-bourbonene can be obtained by a simple operation of direct irradiation with light to the essential oil containing germacrene D. This invention does not necessitate any complicated processes as the prior processes.

By this invention, much amount of $\beta$-bourbonene can be prepared very easily without any use of special and expensive reagent or apparatus, and moreover easily obtainable essential oils can be used as raw material. For the reasons mentioned above, this invention allows economical production of $\beta$-bourbonene.

Furthermore, according to this invention, $\beta$-bourbonene is prepared by direct irradiation of the essential oil, and fractional distillation or refining can be carried out after the formation of $\beta$-bourbonene which is resistant to heat, acid, base, etc. This can extremely reduce the loss of $\beta$-bourbonene. For this reason $\beta$-bourbonene can be obtained with a high yield.

As the preparing process according to this invention is simple, the process is suitable for mass treatment. By addition of the sensitizer and/or by adequate combination of the solvent and the source of the light which is used for irradiation, $\beta$-bourbonene can be prepared in shorter time and with a superior yield.

Owing to many merits which this invention possesses, the invention is extremely fruitful in the industrial production.

The invention will be more clearly understood with reference to the following Examples and Comparative Examples; however, these Examples are not to be construed to limit the scope of the invention.

EXAMPLES 1-9

61.3 kg of leaves of *Solidago altissima L.* was steam-distilled and 123 g of essential oil was obtained. 100 g of the essential oil containing 40 g of germacrene D was subjected to irradiation with light under the prescribed conditions (source of light, method of irradiation, presence and kind of solvent and sensitizer, irradiation time) as shown in Table 1. After completion of reaction, the product was subjected to fractional distillation under reduced pressure and β-bourbonene (b.p. 62° C under 0.4 mm Hg) was obtained. Yield and conversion ratio are also shown in Table 1.

EXAMPLE 10

50 kg of leaves of *Solidago altissima L.* was airdried for 2 days and was soaked for 1 day in 20 l of n-hexane. After filtration, the mixture of about 100 g of the essential oil and 20 l of n-hexane was obtained. The mixture was subjected to internal irradiation with the light of low pressure mercury lamp for 500 hours. After completion of reaction, the reaction product was subjected to fractional distillation under reduced pressure and 32 g of β-bourbonene was obtained.

EXAMPLE 11

The mixture of about 100 g of the essential oil of *Solidago altissima L.* and 20 l of n-hexane was obtained as in example 10. Acetone was added by 1% in volume to the mixture. The mixture containing acetone was irradiated internally with the light of high pressure mercury lamp for 83 hours. The reaction product was subjected to fractional distillation under reduced pressure and 37 g of β-bourbonenewas obtained.

EXAMPLE 12

100 kg of the overground parts of *Solidago altissima L.* was airdried for 2 days and was soaked for 1 day in 20 l of ether. After filtration, the mixture of about 100 g of essential oil and 20 l of ether was obtained. Ethanol was added by 10% in volume to the mixture. The mixture containing ethanol was irradiated internally with the light of high pressure mercury lamp for 117 hours. After completion of reaction, product was subjected to fractional distillation under reduced pressure and 36 g of β-bourbonene was obtained.

Comparison Example 1

100 g of the essential oil of *Solidago altissima L.* was distilled under reduced pressure and 14 g of germacrene D was obtained. 14 g of the germacrene D was dissolved in 2.6 l of n-hexane and the solution thus obtained was subjected to internal irradiation with the light of low pressure mercury lamp for 190 hours. 13 g of β-bourbonene was obtained. In the case of the irradiation with the light of high pressure mercury lamp the similar result was obtained. (Note: The above-mentioned irradiation time is for 14 g of germacrene D. If irradiation is to be given to 100 g of essential oil containing 40 g of germacrene D, irradiation time required will be about 540 hours.)

The results of the above mentioned examples and of comparison example are summarized in Table 1.

TABLE 1

| No. of example | Light Source | Irradiation method | Solvent (Volume Used) | Sensitizer (Quantity Used) | Irradiation time (hr) | Yield (g) | Conversion Ratio(%) |
| --- | --- | --- | --- | --- | --- | --- | --- |
| 1 | LPML*1 | I*2 | — | — | 360 | 29 | 72 |
| 2 | LPML | I | Petroleum ether 200 ml | — | 470 | 33 | 83 |
| 3 | HPML*3 | E*4 | Methanol 100 ml | — | 90 | 32 | 81 |
| 4 | HPML | I | n-Hexane 20 l | Acetophenone 1g | 16 | 40 | 100 |
| 5 | HPML | I | n-Hexane 20 l | Benzophenone 1g | 20 | 40 | 100 |
| 6 | LPML | I | Methanol 20 l | — | 400 | 31 | 78 |
| 7 | HPML | I | n-Hexane 20 l | — | 480 | 26 | 65 |
| 8 | LPML | I | n-Hexane 20 l | Acetophenone 1g | 30 | 39 | 98 |
| 9 | LPML | I | Benzene 20 l | — | 500 | 20 | 50 |
| 10 | LPML | I | n-Hexane 20 l | — | 500 | 32 | 81 |
| 11 | HPML | I | n-Hexane 20 l | Acetone ca. 1 vol.% | 83 | 37 | 92 |
| 12 | HPML | I | Ether 20 l Ethanol 10 vol.% | — | 117 | 36 | 90 |
| Comparison | LPML | I | n-Hexane 2.6 l | — | 190 (540) | 13 | 33 |
| Known | LPML | I | n- | — | Not shown | 3 | 7.5 |

TABLE 1-continued

| No. of example | Light Source | Irradiation method | Solvent (Volume Used) | Sensitizer (Quantity Used) | Irradiation time (hr) | Yield (g) | Conversion Ratio(%) |
|---|---|---|---|---|---|---|---|
| | | | Hexane | | | | |

*[1]LPML: Low pressure mercury lamp
*[2]I: Internal irradiation
*[3]HPML: High pressure mercury lamp
*[4]E: External irradiation Note 1 Figures of the "Known Example" were obtained from the description on the method of Nii et al. (J. Agr. Chem., Japan, Vol. 49, 245 (1975))
Note 2 In "Comparison Example", the figures in parentheses in the column of irradiation time shows the time required for 100 g of essential oil containing 40 g of germacrene D.
Note 3 Yield was calculated on the basis of 100 g of essential oil of Solidago altissima L.
Note 4 Conversion Ratio was calculated according to the following formula:

Conversion Ratio = $\frac{\text{Yield of -bourbonene (g)}}{\text{Quantity of germacrene D (40 g) in essential oil}} \times 100$

EXAMPLES 13–23

100 g of ylang-ylang oil containing 30 g of germacrene D was subjected to irradiation with light under the conditions shown in Table 2 (source of light, method of irradiation, presence and kind of solvent and sensitizer, irradiating time). After completion of reaction, reaction product underwent fractional distillation under reduced pressure and β-bourbonene was obtained. Yield and conversion ratio are also shown in Table 2.

Comparison Example 2

100 g of ylang-ylang oil was subjected to fractional distillation under reduced pressure and 5.4 g of germacrene D was obtained. This was dissolved in 100 ml of acetone with addition of 10 g of xanthone and underwent internal irradiation with the light of high pressure mercury lamp for 40 hours. Reaction product was subjected to fractional distillation under reduced pressure and 4.8 g of β-bourbonene was obtained.

Table 2

| No. of Example | Light Source | Irradiation Method | Solvent (Volume Used) | Sensitizer (Quantity Used) | Irradiation Time (hr) | Yield (g) | Conversion Ratio |
|---|---|---|---|---|---|---|---|
| 13 | LPML*[1] | I*[2] | — | — | 278 | 15 | 50 |
| 14 | LPML | I | Petroleum ether 100 ml | Acetophenone 10 g | 55 | 21 | 70 |
| 15 | LPML | I | Acetone 100 ml | Acetophenone 10 g | 47 | 28 | 93 |
| 16 | LPML | I | Methanol 200 ml | — | 300 | 23 | 77 |
| 17 | HPML*[3] | E*[4] | Benzene 50 ml | — | 300 | 15 | 50 |
| 18 | LPML | I | Ethanol 100 ml | — | 300 | 23 | 77 |
| 19 | HPML | I | — | Acetophenone 10 g | 46 | 21 | 70 |
| 20 | HPML | I | Acetone 100 ml | m-Methoxy acetophenone 10 g | 43 | 23 | 77 |
| 21 | HPML | I | n-Hexane 100 ml | — | 300 | 25 | 83 |
| 22 | HPML | I | n-Hexane 100 ml | Benzophenone 10 g | 50 | 23 | 77 |
| 23 | HPML | I | Acetone 100 ml | Xanthone 10 g | 40 | 25 | 83 |
| Comparison 2 | HPML | I | Acetone 100 ml | Xanthone 10 g | 40 | 4.8 | 16 |

*[1]LPML: Low pressure mercury lamp
*[2]I: Internal irradiation
*[3]HPML: High pressure mercury lamp
*[4]E: External irradiation Note 5 Sampling was made every fixed hour and quantity of inconverted germacrene D was analysed by gas chromatography. By the results of the analysis, optimum irradiation time was determined.
Note 6 Yield was calculated on the basis of 100 g of ylang-ylang oil containing 30 g of germacrene D.
Note 7 Conversion ratio was calculated according to the following formula:

Conversion Ratio = $\frac{\text{Yield of }\beta\text{-bourbonene (g)}}{\text{Quantity of germacrene D (30 g) in essential oil}} \times 100$

EXAMPLE 24

60 kg of leaves of *Solidago gigantea Aiton var. leiophylla Fern.* was steam-distilled and 120 g of essential oil was obtained. 100 g of the essential oil containing 40 g of germacrene D was dissolved in 20 l of n-hexane with addition of 50 g of acetophenone and was subjected to internal irradiation with the light of high pressure mercury lamp for 12 hours. After fractional distillation under reduced pressure, 37 g of β-bourbonene was obtained. (Conversion Ratio: 93%)

EXAMPLE 25

60 kg of leaves of *Solidago viragaurea L. subsp. asiatica Kitamura* was steam-distilled and 102 g of essential oil was obtained. 100 g of the essential oil containing 30 g of germacrene D was dissolved in 20 l of n-hexane with addition of 50 g of acetophenone and was subjected to internal irradiation with the light of high pressure mercury lamp for 10 hours. 25 g of β-bourbonene was obtained by fractional distillation under reduced pressure. (Conversion Ratio: 83%)

As can be seen from the results of the examples according to the invention mentioned above, β-bourbonene could be obtained with high conversion ratio in all cases. By adequate selection of solvent and addition of sensitizer, β-bourbonene was obtained from essential oil with higher conversion ratio. It was also found that irradiation time could be much reduced by the addition of sensitizer. In the case of the comparison examples and the known example which comprise of isolating germacrene D from the essential oil and irradiating the isolated germacrene D with light to obtain β-bourbonene, the ratio of conversion of germacrene D to β-bourbonene is extremely low and thus β-bourbonene could only be obtained with very low yield.

What we claim is:

1. Process for preparing β-bourbonene which comprises irradiating an essential oil containing germacrene D, with light to obtain β-bourbonene.

2. Process for preparing β-bourbonene as claimed in claim 1, wherein a mercury lamp is used as the light source.

3. Process for preparing β-bourbonene as claimed in claim 1, wherein the essential oil containing germacrene D is at least one selected from the group consisting of ylang-ylang oil, cananga oil, essential oil obtained from *Solidago altissima L.*, essential oil obtained from *Solidago gigantea Aiton var. leiophylla Fern.*, and essential oil obtained from *Solidago viragaurea L.* subsp. *asiatica Kitamura*.

4. Process for preparing β-bourbonene as claimed in claim 1, wherein ketone is added as sensitizer to the essential oil containing germacrene D.

5. Process for preparing β-bourbonene as claimed in claim 3, wherein the ketone is at least one from the group consisting of acetone, di-t-butyl ketone, acetophenone, benzophenone, cyclohexanone, menthonl, xanthone, anthraquinone and methoxyacetophenone.

6. Process for preparing β-bourbonene as claimed in claim 1, wherein at least one solvent selected from the group consisting of petroleum ether, petroleum benzine, ligroin, hexane, cyclohexane, ether, benzene, ethyl acetate, methanol, ethanol, acetonitrile and water is added to the essential oil containing germacrene D.

7. Process for preparing β-bourbonene as claimed in claim 6, wherein the essential oil containing at least one solvent selected from the group consisting of petroleum ether, hexane, acetone, methanol and ethanol is irradiated with the light of low pressure mercury lamp.

8. Process for preparing β-bourbonene as claimed in claim 6, wherein the essential oil containing at least one solvent selected from the group consisting of methanol, ethanol and acetone is irradiated with the light of high pressure mercury lamp.

* * * * *